US008030461B2

(12) United States Patent
Kojima

(10) Patent No.: US 8,030,461 B2
(45) Date of Patent: Oct. 4, 2011

(54) METHODS FOR CONSTRUCTING SCDB LIBRARIES

(75) Inventor: Tetsuo Kojima, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 292 days.

(21) Appl. No.: 10/510,971

(22) PCT Filed: Apr. 15, 2003

(86) PCT No.: PCT/JP03/04773
§ 371 (c)(1),
(2), (4) Date: Jun. 21, 2005

(87) PCT Pub. No.: WO03/087163
PCT Pub. Date: Oct. 23, 2003

(65) Prior Publication Data
US 2007/0087381 A1  Apr. 19, 2007

(30) Foreign Application Priority Data

Apr. 15, 2002 (JP) ................................. 2002-112369

(51) Int. Cl.
*C07H 21/04* (2006.01)
(52) U.S. Cl. ..................................................... 536/23.1
(58) Field of Classification Search .................. 536/23.1
See application file for complete search history.

(56) References Cited

U.S. PATENT DOCUMENTS

| 7,129,330 B1 | 10/2006 | Little et al. |
| 2004/0219643 A1 | 11/2004 | Winter et al. |
| 2006/0159673 A1 | 7/2006 | Kojima |
| 2006/0269989 A1 | 11/2006 | Miyazaki et al. |

FOREIGN PATENT DOCUMENTS

| CA | 2 331 641 | 11/1999 |
| DE | 198 19 846 | 11/1999 |
| EP | 0 774 511 | 5/1997 |
| JP | 2001-523971 | 11/2001 |
| WO | WO 96/34892 | 11/1996 |
| WO | WO 98/50431 | 11/1998 |
| WO | WO 99/57150 | 11/1999 |
| WO | WO 00/44788 | 8/2000 |
| WO | WO 01/44282 | 6/2001 |
| WO | WO 01/70775 | 9/2001 |
| WO | WO 03/087163 | 10/2003 |

OTHER PUBLICATIONS

Cekaite et al. Methods Mol Biol. 360:335-348 (2007).*
McGuinness et al. (Nat. Biotech. 14:1149-1154 (1996)).*
MacCallum et al. (J. Mol. Biol. (1996) 262:732-745).*
Pascalis et al. The Journal of Immunology (2002) 169, 3076-3084.*
Casset et al. (2003) BBRC 307, 198-205.*
Vajdos et al. (2002) J. Mol. Biol. 320, 415-428.*
Holm et al (2007) Mol. Immunol. 44: 1075-1084.*
Chen et al. J. Mol. Bio. (1999) 293, 865-881.*
Wu et al. J. Mol. Biol. (1999) 294, 151-162.*
Smith-Gill et al. (J. Immunol. 139:4135-4144 (1987)).*
Song et al. (Biochem Biophys Res Comm 268:390-394 (2000)).*
Kumar et al. (J. Biol. Chem. 275:35129-35136 (2000)).*
Clarkson et al. (Nature 352:624-628 (1991)).*
Rousch et al., Br. J. Pharmacol., 125: 5-16 (1998).*
New England Biolabs list of restriction enzymes (pp. 1-3, Dec. 30, 2009).*
Desplancq et al. (Protein Engineering 7:1027-1033 (1994)).*
Kim et al. (Protein Engineering, Design & Selection 20(9):425-432 (2007)).*
Carter, "Bispecific human IgG by design," *J. Immunol. Methods*, 248:7-15 (2001).
De Jonge et al., "Production and Characterization of Bispecific Single-Chain Antibody Fragments," *Mol. Immunol.*, 32:1405-1412 (1995).
Hoogenboom et al., "Multi-subunit proteins on the surface of filamentous phage: methodologies for displaying antibody (Fab) heavy and light chains," *Nucleic Acids Res.*, 19:4133-4137 (1991).
Hudson et al., "High avidity scFv multimers; diabodies and triabodies,"*J. Immunol. Methods*, 231:177-189 (1999).
Kipriyanov et al., "Effect of Domain Order on the Activity of Bacterially Produced Bispecific Single-chain Fv Antibodies," *J. Mol. Biol.*, 330:99-111 (2003).
Krebber et al., "Reliable cloning of functional antibody variable domains from hybridomas and spleen cell repertoires employing a reengineered phage display system," *J. Immunol. Methods*, 201:35-55 (1997).
Kurucz et al., "Retargeting of CTL by an Efficiently Refolded Bispecific Single-Chain Fv Dimer Produced in Bacteria,"*J. Immunol.*, 154:4576-4582 (1995).
Little et al., "Of mice and men: hybridoma and recombinant antibodies," *Immunol. Today*, 21:364-370 (2000).
Merchant et al., "An efficient route to human bispecific IgG," *Nat. Biotechnol.*, 16:677-681 (1998).
Peipp et al., "Bispecific antibodies targeting cancer cells," *Biochem. Soc. Trans.*, 30:507-511 (2002).
Plückthun et al., "New protein engineering approaches to multivalent and bispecific antibody fragments," *Immunotechnology*, 3:83-105 (1997).
Ridgway et al., "'Knobs-into-holes' engineering of antibody $C_H3$ domains for heavy chain heterodimerization," *Protein Eng.*, 9:617-621 (1996).
Shalaby et al., "Development of Humanized Bispecific Antibodies Reactive with Cytotoxic Lymphocytes and Tumor Cells Overexpressing the *HER2* Protooncogene," *J. Exp. Med.*, 175:217-225 (1992).
Skerra, "Use of the tetracycline promoter for the tightly regulated production of a murine antibody fragment in *Escherichia coli*," *Gene*, 151:131-135 (1994).
Völkel et al., "Optimized linker sequences for the expression of monomeric and dimeric bispecific single-chain diabodies," *Protein Eng.*, 14:815-823 (2001).
Zuo et al., "An efficient route to the production of an IgG-like bispecific antibody," *Protein Eng.*, 13:361-367 (2000).
Supplemental IPER (Apr. 10, 2006).
Goldstein et al., "Cytolytic and Cytostatic Properties of an Anti-Human FcγRI (CD64)×Epidermal Growth Factor Bispecific Fusion Protein," *J. Immunol.*, 158:872-879 (1997).

(Continued)

*Primary Examiner* — Lynn Bristol
(74) *Attorney, Agent, or Firm* — Fish & Richardson P.C.

(57) ABSTRACT

Bispecific diabody libraries can be constructed from scFv libraries efficiently and without troublesome procedures by a single treatment, placing restriction enzyme sites appropriately for antigen-encoding regions.

12 Claims, 2 Drawing Sheets

OTHER PUBLICATIONS

McGuinness BT et al., "Phage diabody repertoires for selection of large number of bispecific antibody fragments", Nature Biotechnology, vol. 14(9), pp. 1149-1154 (1996).

DeNardo D.G. et al., "Anti-HLA-DR/anti-DOTA diabody construction in modular gene design platform: bispecific antibodies for pretargeted radioimmunotherapy", Cancer Biotherapy & Radiopharmaceuticals, vol. 16(6), pp. 525-535 (2001).

Andris-Widhopf J. et al., "Methods for the generation of chicken monoclonal antibody fragments by phage display", Journal of Immunological Methods, vol. 242, pp. 159-181 (2000).

Turner D.J. et al., "Importance of the linker in expression of single-chain Fv antibody-fragments: optimization of peptide sequence using phage display technology", Journal of Immunological Methods, vol. 205, pp. 43-54 (1997).

Tang Y. et al., "Selection of linkers for a catalytic single-chain antibody using phage display technology", The Journal of Biological Chemistry, vol. 271(26), pp. 15682-15686 (1996).

Holliger P. et al., "'Diabodies', small bivalent and bispecific antibody fragments", Proc. Natl. Acad. Sci. USA, vol. 90, pp. 6444-6448 (1993).

Cekaite et al., "Protein Arrays: A versatile toolbox for target identification and monitoring of patient immune responses", Methods Mol. Biol., 360:335-348, 2007.

Kipriyanov and Little, "Generation of Recombinant Antibodies," *Molecular Biotechnology*, 12:173-201 (1999).

\* cited by examiner

SEQUENCE LISTING

<160> NUMBER OF SEQ ID NOS: 6

<210> SEQ ID NO 1
<211> LENGTH: 60
<212> TYPE: DNA
<213> ORGANISM: Artificial Sequence
<220> FEATURE:
<223> OTHER INFORMATION: Description of Artificial Sequence:linker

<400> SEQUENCE: 1
ggtggtggtg gatccggtgg tggtggttct ggcggcggcg gctccggagg tggtggttct    60

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence:linker

<400> SEQUENCE: 2

Gly Gly Gly Gly Ser Gly Gly Gly Gly Ser Gly Gly Gly Gly Ser Gly
 1               5                  10                  15

Gly Gly Gly Ser

```
<210> SEQ ID NO 3
<211> LENGTH: 60
<212> TYPE: DNA
<213> ORGANISM: Artificial Sequence
<220> FEATURE:
<223> OTHER INFORMATION: Description of Artificial Sequence:linker

<400> SEQUENCE: 3
ggtggtggtg gatccggtgg tggtggttct ggcggcggcg gctccggagg tggtggatcc     60

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence:linker

<400> SEQUENCE: 4

Gly Gly Gly Gly Ser Gly Gly Gly Gly Ser Gly Gly Gly Gly Ser Gly
 1               5                  10                  15

Gly Gly Gly Ser
            20

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence:linker

<400> SEQUENCE: 5
ggtggtggtg gatcc                                                      15

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence:linker

<400> SEQUENCE: 6

Gly Gly Gly Gly Ser
 1               5
```

METHODS FOR CONSTRUCTING SCDB LIBRARIES

TECHNICAL FIELD

The present invention relates to single chain diabody (scDb) libraries and to methods for constructing such libraries. The present invention also relates to genes comprised in such scDb libraries, expression vectors comprising these genes, and methods for constructing these genes and vectors. The invention further relates to peptides encoded by these genes.

BACKGROUND ART

Multi-specific antibodies, capable of binding to different antigens (bispecific antibodies (bsAb), for example), are useful in clinical fields such as immunodiagnosis, immunotherapy, and diagnosis based on immunoassays. For example, multi-specific antibodies can be used for immobilizing enzymes used for enzyme immunoassays. In such cases, one arm of a multi-specific antibody is designed to bind to an epitope on an enzyme region that does not interfere with the enzyme reaction. The other arm is designed to bind to an immobilizing carrier, so that the enzyme is immobilized on the carrier via the antibody (Hammerling et al., J. Exp. Med. 128: 1461-1473 (1968)). In addition, it has been reported that multi-specific antibodies can be used for immunodiagnosis of a variety of diseases, including cancers (Songsivilai et al., Clin. Exp. Immunol. 79: 315-321 (1990)). For example, bispecific antibodies used for cancer diagnosis are designed such that one arm of the antibody recognizes a tumor-related antigen, and the other arm binds to a detectable marker (for example, Le Doussal et al., Int. J. Cancer Suppl. 7: 58-62 (1992); Le Doussal et al., J. Nucl. Med. 34: 1662-1671 (1993); Stickney et al., Cancer Res. 51: 6650-6655 (1991)).

Furthermore, in patients, multi-specific antibodies are known to be used for inducing cellular immune responses against pathogens or tumor cells (Segal and Snider, Chem. Immunol. 47: 179-213 (1989); Segal et al., Biologic Therapy of Cancer 2(4) De Vita et al. eds., J. B. Lippomcott, Philadelphia (1992) p. 1; Hsieh-Ma et al., Cancer Res. 52: 6832-6839 (1992); Weiner et al., Cancer Res. 53: 94-100 (1993)). Multi-specific antibodies can also be designed to induce T-cell-mediated cytotoxicity (Shalaby et al., J. Exp. Med. 175(1): 217-225 (1992); de Liji et al., "Bispecific Antibodies and Targeted Cellular Cytotoxicity", Romet-Lemonne, Fanger and Segal eds., Lienhart (1991) p. 249; Clark et al., "Bispecific Antibodies and Targeted Cellular Cytotoxicity", Romet-Lemonne, Fanger and Segal Eds. Lienhart (1991) p. 243; Kroesen et al., Cancer Immunol. Immunother. 37: 400-407 (1993); Kroesen et al., Br. J. Cancer 70: 652-661 (1994); Weiner et al., J. Immunol. 152: 2385-2392 (1994)). Moreover, multi-specific antibodies can be used as fibrinolytic agents or vaccination adjuvants, and also for treatment of infectious diseases (for example, targeting cells infected with HIV, influenza, trypanosomes, and such), delivering antitoxins to tumor cells, and bringing immune complexes to cell surface receptors (Fanger et al., as described above).

Conventionally, multi-specific antibodies were produced by methods such as (1) chemical coupling of different antibodies with distinct specificities using hetero-bifunctional linkers (Paulus, Behring Inst. Mitt., 78:118-132 (1985)); (2) fusion of hybridoma cells secreting different monoclonal antibodies (Milstein and Cuello, Nature 305: 537-539 (1983)); and (3) transfection of genes encoding light chains and heavy chains of different monoclonal antibodies (four genes) into mouse myeloma cells or other eukaryotic expression systems, followed by isolating monovalent portions with bispecificity (Zimmermann, Rev. Physiol. Biochem. Pharmacol. 105: 176-256 (1986); van Dijk et al., Int. J. Cancer 43: 944-949 (1989)).

Diabodies (Db) are bivalent antibody fragments constructed by gene fusion (Holliger P. et al., Proc. Natl. Acad. Sci. USA 90: 6444-6448 (1993); EP 404,097; WO93/11161). Diabodies are dimers comprising two polypeptide chains, where each polypeptide chain comprises a light chain variable domain ($V_L$) and a heavy chain variable domain ($V_H$) connected with a linker short enough to prevent interaction of these two domains, for example a linker of about five amino acids. The $V_L$ and $V_H$ domains encoded on the same polypeptide chain will form a dimer because the linker between the $V_L$ and $V_H$ is too short to form a single chain variable region fragment (scFv). Thus, the result is a diabody that comprises two antigen-binding sites. If the $V_L$ and $V_H$ domains directed against two different antigens (a and b) are expressed simultaneously as combinations of $V_L$a-$V_H$b and $V_L$b-$V_H$a connected with a linker of about five residues, they can be secreted as a bispecific diabody. Bispecific diabodies are a type of multi-specific antibody.

SUMMARY OF THE INVENTION

Since there are three ways to combine two types of chains, the yield of bispecific diabodies is limited to 50% of the total. On the other hand, when using phage antibody libraries to select particular genes based on their antigen reactivity, the $V_H$ and $V_L$ domains must be connected with a linker of about 15 residues and expressed in order to present the antigen-binding site as an scFv. Therefore, after using antigen binding to select the $V_H$ and $V_L$ domains of an scFv from a phage antibody library, complicated manipulations such as PCR assembly are required to express these domains as bispecific scDbs. Such complicated manipulations are needed to change the linker length from about 15 residues, as required for scFv expression, to about five residues, which enables diabody expression. This makes it difficult to collectively express the $V_H$ and $V_L$ domains of scFvs as bispecific scDbs.

The present invention provides novel methods for constructing bispecific scDb libraries. The present invention produces bispecific diabodies with certainty, by expressing $V_H$ and $V_L$ domains directed against two different antigens (a and b) as a single chain in the order $V_L$a-$V_H$b-$V_L$b-$V_H$a, with a linker of 15 or more residues between $V_H$b and $V_L$b. (However, the present invention is not limited by the order of the variable domains such as $V_L$a, $V_H$a, $V_L$b, and $V_H$b). In the present invention, bispecific scDb libraries expressing such polypeptide chains ($V_L$a-$V_H$b-$V_L$b-$V_H$a) can be constructed in one step from scFv phage libraries. Specifically, two genes are prepared. First gene comprises nucleotides encoding two antibody variable domains ($V_L$a and $V_H$a) connected by a linker containing a restriction enzyme site. Second gene comprises nucleotides encoding two antibody variable domains ($V_L$b and $V_H$b) connected by a long linker, comprising restriction enzyme sites at the nucleotide ends not connected to the linker. The genes are treated with restriction enzymes, and then combined by ligation to place the $V_L$b and $V_H$b between the $V_L$a and $V_H$a. In addition to methods for constructing bispecific scDb libraries, the present invention provides genes used in the methods, genes obtained by the methods, expression vectors or antibody libraries comprising these genes, and peptides encoded by these genes.

In addition, as methods for collectively expressing, as bispecific scDbs, scFv $V_H$ and $V_L$ domains selected by antigen binding, the present invention provides methods for collectively transferring antibody clones concentrated by panning and such, from a phage antibody library into expression vectors for use in animal cells. More specifically, the present invention relates to:

(1) a gene encoding two antibody variable domains, wherein the two antibody variable domains are connected by a linker comprising a restriction enzyme site;

(2) the gene of (1), wherein the linker comprises two or more restriction enzyme sites;

(3) the gene of (1) or (2), wherein one of the two antibody variable domains is a heavy chain variable domain and the other is a light chain variable domain;

(4) the gene of any one of (1) to (3), wherein the two antibody variable domains are connected by a long linker;

(5) a gene encoding two antibody variable domains, where both ends comprise a restriction enzyme site;

(6) the gene of (5), wherein one of the two antibody variable domains is a heavy chain variable domain and the other is a light chain variable domain;

(7) the gene of (5) or (6), wherein the two nucleotides encoding the two antibody variable domains are connected with a long linker;

(8) a gene encoding four antibody variable domains, wherein the gene comprises a restriction enzyme site between the first and second antibody variable domains, and between the third and fourth antibody variable domains;

(9) the gene of (8), wherein the first and second antibody variable domains are connected with a short linker, the third and fourth domains are connected with a short linker, and the second and third antibody variable domains are connected with a long linker;

(10) the gene of (8) or (9), wherein the four antibody variable domains are a heavy chain variable domain and a light chain variable domain directed against a first antigen, and a heavy chain variable domain and a light chain variable domain directed against a second antigen;

(11) the gene of (10), wherein the four antibody variable domains are comprised in the order: a light chain variable domain against the first antigen, a heavy chain variable domain directed against the second antigen, a light chain variable domain against the second antigen, and a heavy chain variable domain against the first antigen;

(12) a method for constructing a gene encoding a bispecific single chain diabody, wherein the method comprises:
  (a) treating the gene of any one of (1) to (4) with a restriction enzyme;
  (b) treating the gene of any one of (5) to (7) with a restriction enzyme; and
  (c) inserting the gene constructed in step (b) into the gene constructed in step (a);

(13) a peptide encoded by a gene of any of (1) to (11);

(14) an antibody library comprising a gene of any of (1) to (11);

(15) a method for constructing an antibody library or expression vector, wherein the method comprises:
  (a) constructing an antibody phage library in which a light chain variable domain and a heavy chain variable domain, both directed against a first antigen, are connected with a long linker comprising a restriction enzyme site;
  (b) constructing an antibody phage library in which a light chain variable region and a heavy chain variable domain, both directed against a second antigen, are connected with a long linker at one end, where the other ends comprise a restriction enzyme site;
  (c) treating the phage libraries constructed in steps (a) and (b), or genes comprising the variable domains prepared from these phage libraries, with a restriction enzyme; and
  (d) performing ligation of the fragments obtained from the above treatment to construct a fragment in which the heavy and light chain variable domains against the second antigen are inserted between the light and heavy chain variable domains against the first antigen;

(16) a method for constructing an antibody library or expression vector, wherein the method comprises:
  (a) treating the gene of any one of (1) to (4) with a restriction enzyme;
  (b) treating the gene of any one of (5) to (7) with a restriction enzyme; and
  (c) inserting the gene constructed in step (b) into the gene constructed in step (a);

(17) a method for constructing an antibody library or expression vector, wherein the method comprises:
  (a) constructing an antibody phage library in which a light chain variable domain and a heavy chain variable domain, both against an antigen, are connected with a long linker comprising two or more restriction enzyme sites;
  (b) treating the above phage library, or genes comprising variable domains prepared from the phage library, with a restriction enzyme; and
  (c) performing self-ligation of the fragments obtained above to shorten the linker between the variable domains; and

(18) an expression vector comprising a gene of any one of (1) to (11).

DETAILED DESCRIPTION

The methods of the present invention can be applied not only to screening bispecific scDbs, but also for screening monospecific scDbs (for example, scDbs comprising the variable domains of different sequences but still able to recognize the same epitope).

Figure 1:
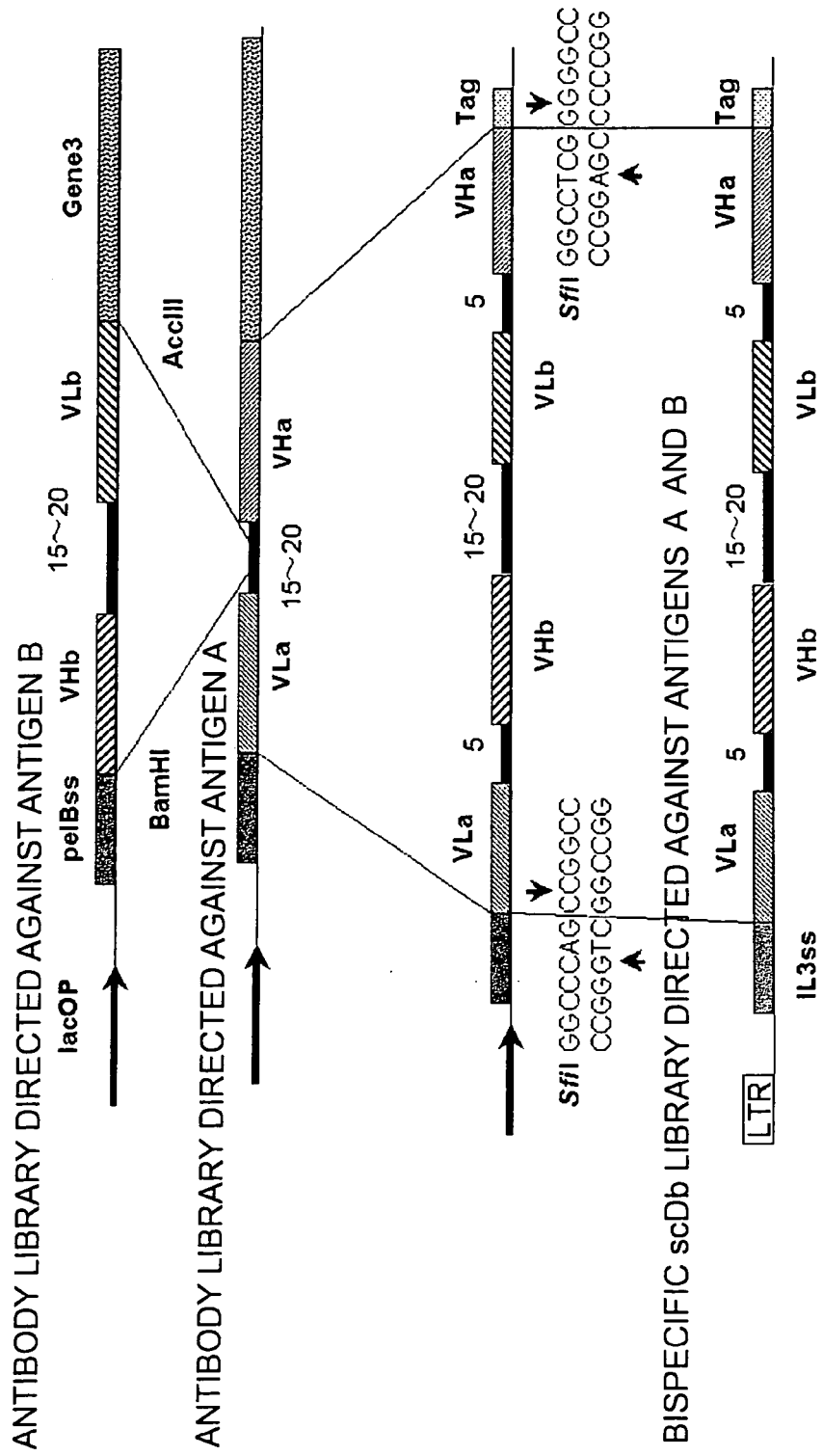
FIG. 1 schematically shows a method for constructing a bispecific scDb library directed against antigens A and B.
Figure 2:
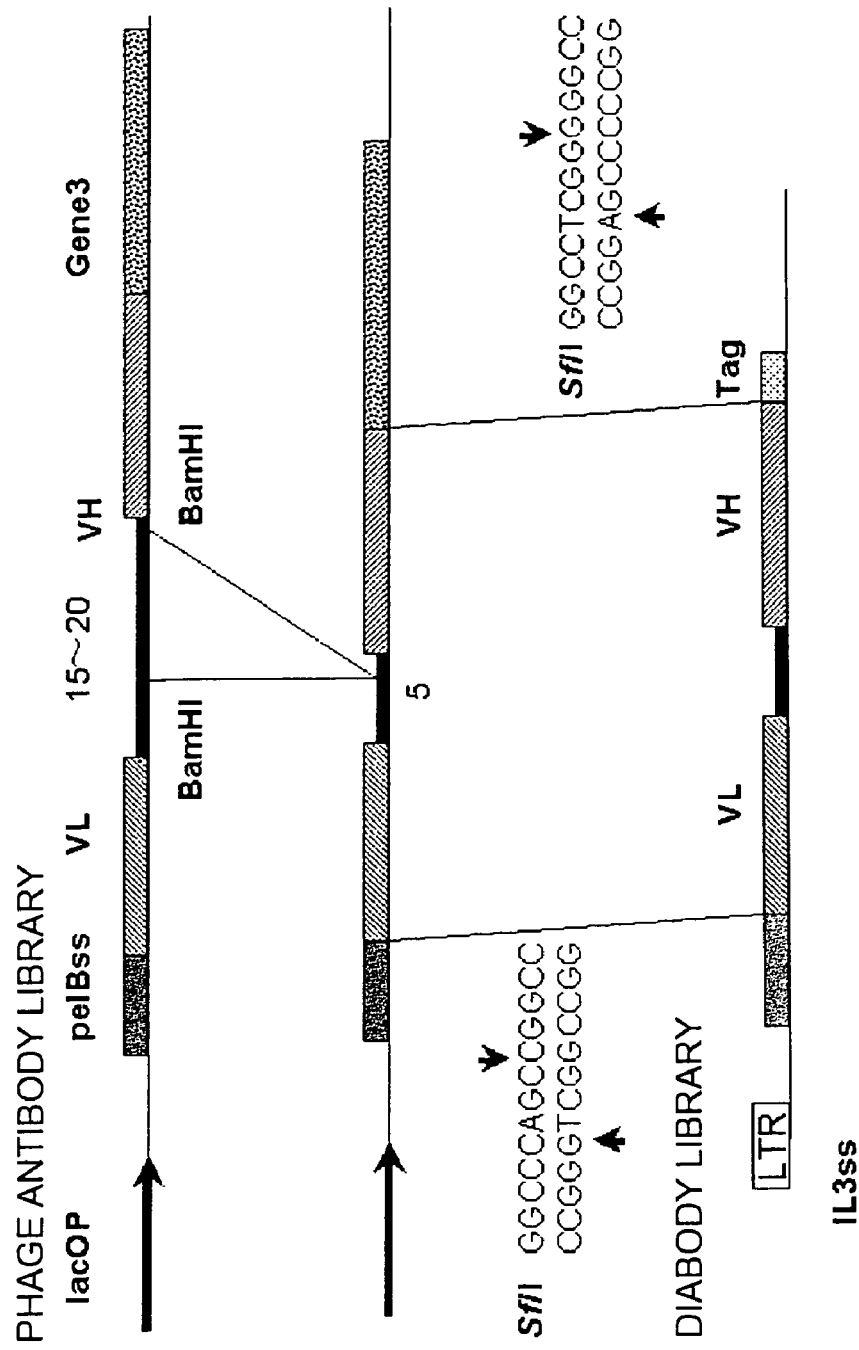
FIG. 2 schematically shows a method for constructing a diabody library from a phage antibody library.

In the methods for constructing scDb libraries of the present invention, as shown in FIG. 1, for example, an antibody phage library is first constructed from spleens and such of animals immunized with antigen A. The library is constructed such that the variable domains are linked in the order of $V_L$-$V_H$. Antibody phage libraries can be constructed according to known methods (for example, McCafferty et al., Nature 348: 552-554 (1990); Clackson et al., Nature 352: 624-628 (1991); Marks et al., J. Mol. Biol. 222: 582-597 (1991)).

Examples of antigens used for animal immunization are complete antigens with immunogenicity, and incomplete antigens (including haptens) without immunogenicity. Antigens may be substances consisting of proteins, polypeptides, polysaccharides, nucleic acids, lipids, etc. However, in the present invention, the type of substance that may constitute an antigen is not restricted. Immunogens used for immunizing animals may also be antigens that can solubilize on conjugation with other molecules. They can also be antigen fragments. When transmembrane molecules such as receptors are used as antigens, a fragment thereof may be preferably used (an extracellular domain of the receptor, for example). In addition, cells expressing transmembrane molecules on their surface can be used as immunogens. Such cells may be those obtained naturally (tumor cell lines, etc.), or those designed to express transmembrane molecules using recombinant technology.

Bispecific diabodies can be used in the same manner as conventionally known bispecific antibodies. Therefore, for treatment of cancers, for example, bispecific diabodies may be designed such that one arm recognizes a tumor cell antigen and the other recognizes a molecule capable of inducing cytotoxicity. In this case, tumor cell antigens can be selected from molecules such as CD15, p185$^{HER2}$, 1D10 (malignant B cell), p97, renal cell carcinoma, OVCAR-3, L-D1 (colon cancer), melanocyte stimulating hormone analogue, EGF receptor, CAMA1, MoV18, CD19, NCAM (neural cell adhesion molecule), FBP (folic acid binding protein), AMOC-31 (pan carcinoma associated antigen), Id-1, CD22, CD7, CD38, and CEA. Molecules capable of inducing cytotoxicity may be FcγRI, CD16, and CD3. Alternatively, in place of the above cytotoxicity-inducing molecules, diabodies can be designed to bind to toxins such as saponin, ricin A chain, IFN-α, and vinca alkaloids. Such bispecific diabodies are extremely useful in the treatment of cancers.

In addition, bispecific diabodies are useful as agonist antibodies. For example, many cytokine receptors are known to exist as homo- or hetero-dimers, and it is thought that ligand binding induces a change in distances and angles between the chains involved in dimer formation, and elicits signal transduction inside cells. Thus, bispecific diabodies capable of binding to such receptor dimers can mimic ligand-induced dimerization of the receptor, and therefore function as agonist diabodies.

In another embodiment, bispecific diabodies may be (1) diabodies involving enzymes that promote substance conversion, such as diabodies that bind to CD30 and alkaline phosphatase, thereby converting mitomycin phosphate to mitomycin alcohol; (2) diabodies that can be used as fibrinolytic agents, such as those that bind to fibrin, tPA, uPA, and such; (3) diabodies delivering an immune complex to cell surface receptors by binding to an LDL receptor, Fc receptor (FcγRI, FcγRII or FcγRIII), and such; and (4) diabodies used for treatment of infectious diseases, recognizing T-cell antigens such as CD3, and antigens from pathogens such as HCV, influenza, and HIV; (5) diabodies capable of binding to tumor antigens that can be used for tumor detection, and detectable compounds such as EOTUBE, DPTA, and haptens; and (6) diabodies that can be used as vaccination adjuvants (Fanger et al., Crit. Rev. Immunol. 12: 101-124 (1992)); and (7) diabodies that can be used for diagnosis, directed against a detectable compound such as rabbit IgG, horse radish peroxidase (HRP), FITC, and β-galactosidase, and against antigens such as hormones, ferritin, somatostatin, substance P, and CEA. However, the diabodies of the present invention are not limited thereto.

Next, antigens are used to immunize suitable mammals. For example, mice, hamsters, or rhesus monkeys can be used for immunization. Alternatively, lymphocytes can be immunized in vitro. Subsequently, DNAs encoding antibodies that are comprised in the lymphocytes or in the spleens of immunized animals are isolated according to well-known methods (for example, using a nucleotide probe capable of binding specifically to genes encoding antibody heavy chains and light chains).

Herein, heavy chain and light chain variable domains mean portions of immunoglobulin heavy chains and light chains that comprise usually about 110 amino acids from the N-terminus. Immunoglobulins are classified into different classes (IgA, IgD, IgE, IgG, and IgM), which are further classified into several subclasses (isotypes; IgG-1, IgG-2, IgG-3, and IgG-4, and IgA-1, and IgA-2, for example). The heavy chain and light chain variable domains of the present invention may belong to any of the above classes and subclasses, and are not specifically limited.

The antibody variable domains of the present invention may be shortened or altered antibody fragments, as long as they comprise the ability to bind to a desired antigen. An "Fv" fragment is a minimal antibody fragment, comprising a complete antigen recognition site and binding site. This domain is a dimer comprising heavy chain and light chain variable domains strongly connected by non-covalent bonds. Three complementarity determining regions (CDRs; hyper variable regions) in each variable domain interact with each other to form antigen binding sites on the dimer surface. Thus, on combining the heavy chain and light chain, an antibody has six CDRs functioning as antigen binding sites. However, it is known that a single variable domain is still capable of recognizing and binding to an antigen, albeit with a lower affinity than when including all binding sites. Therefore, it is especially preferred that the antibody variable domains making up the diabodies of the present invention are Fv fragments, but they are not limited thereto, as long as they retain a CDR from a heavy chain or light chain, and can recognize and bind to an antigen.

In addition, a technology using gene engineering to create "humanized antibodies" is known. In this technology, all but the CDR of monoclonal antibodies from non-human mammals (such as mice, rats, and hamsters) is replaced with frame structure sequences of variable domains from human immunoglobulins (see for example, Jones et al., Nature 321: 522-525 (1986); Riechmann et al., Nature 332: 323-329 (1988); Presta, Curr. Op. Struct. Biol. 2: 593-596 (1992)). Humanized antibodies may comprise amino acids that are comprised in neither the CDR introduced into the recipient antibody nor the frame structure sequences. Normally, such introduction of amino acid residues is performed to optimize antibodies for more precise antigen recognition and binding. The variable domain of the present invention also comprises altered variable domains, such as humanized domains.

In addition, other regions of the variable domain can be altered to improve biological features of antibodies, such as antigen binding. Such alterations can be performed using site-directed mutagenesis (Kunkel, Proc. Natl. Acad. Sci. USA 82: 488 (1985), PCR mutagenesis, cassette mutation, and such. In general, mutated antibodies with improved biological features have an amino acid sequence with a homology or similarity of 70% or higher, preferably 80% or higher, and more preferably 90% or higher (for example, 95% or higher) compared to the original antibody heavy chain or light chain variable domain. Herein, sequence homology or similarity is defined as the percentage of amino acids that are homologous (having the same residues) or similar (having residues categorized into the same group based on general features of the side chain) to the original residues, determined after conducting any alignment of sequences and introduction of gaps necessary to obtain the maximal sequence homology.

Natural amino acid residues are usually categorized, based on the characteristics of their side chain, into (1) hydrophobic residues: norleucine, methionine, alanine, valine, leucine, and isoleucine; (2) neutral hydrophilic residues: cysteine, serine, threonine, asparagine, and glutamine; (3) acidic residues: aspartic acid, and glutamic acid; (4) basic residues: histidine, lysine, and arginine; (5) residues influencing chain orientation: glycine and proline; and (6) aromatic residues: tryptophan, tyrosine, and phenylalanine.

Subsequently, the isolated DNAs encoding the heavy and light chains are connected with a linker of about 20 residues, and cloned into an appropriate phage vector to construct a phage library. The linker is designed to comprise recognition sites for restriction enzymes such as BamHI and AccIII. Such linkers may comprise, for example, the following sequences:

```
             BamHI                                    AccIII
GGTGGTGGTGGATCCGGTGGTGGTGGTTCTGGCGGCGGCGGCTCCGGAGGTGGTGGTTCT  (SEQ ID NO: 1)

CCACCACCACCTAGGCCACCACCACCAAGACCGCCGCCGCCGAGGCCTCCACCACCAAGA

GlyGlyGlyGlySerGlyGlyGlyGlySerGlyGlyGlyGlySerGlyGlyGlyGlySer  (SEQ ID NO: 2)
```

The restriction enzyme recognition sites used in the method of the present invention may be those for BamHI, AccIII, AluI, EcoRI, HincII, HindIII, HinfI, NotI, SacI, SalI, Sau3AI, SmaI, TaqI, XbaI, AatI, BclI, BstEII, EheI, KpnI, NheI, PstI, PvuII, SfiI, BglI, HaeIII, HhaI, HpaII, XhoI, and such.

In addition, phages constituting a phage library may be G4 phages, M13 phages, fd phages, f1 phages, λ phages, T4 phages, T7 phages, P1 phages, MS2 phages, ΦK phages, ΦX174 phages, λgWES, λB, Charon 4A, Charon 30, and such.

Similarly, an antigen different to antigen A, or the same antigen (aimed at a different epitope, for example) is used to immunize animals or lymphocytes; DNAs encoding antibody heavy chains or light chains are isolated; and an antibody phage library is constructed in which the variable domains are connected, in the order of $V_H$-$V_L$, with a linker of about 20 residues. Therein, the 5'-terminus of $V_H$b and the 3'-terminus of $V_L$b are designed to comprise recognition sites for restriction enzymes so that the genes encoding $V_H$b and $V_L$b, which can bind antigen B, are inserted between the genes encoding $V_L$a and $V_H$a, which can bind antigen A. Thus, if a library for antigen A is constructed using BamHI and AccIII recognition sites, the 5'-terminus of $V_H$ and the 3'-terminus of $V_L$ are designed to comprise BamHI and AccIII, respectively.

Next, the above phage libraries, or genes prepared from these phage libraries and comprising the variable domains (for example, phagemids concentrated by panning and such from the respective libraries (e.g. Vaughan et al., Nature Biotechnology 14: 309-314 (1996)), or genes amplified by PCR from the above phage libraries) are treated with the restriction enzymes whose recognition sites were placed in the linker and terminals of the genes encoding $V_H$ and $V_L$. For example, in the above case, where the linker comprises recognition sites for BamHI and AccIII, treatment is with BamHI and AccIII. The obtained genes, which encode $V_H$-$V_L$ antibody fragments against antigen B, are inserted between the BamHI and AccIII sites of the antibody phagemid against antigen A. In this way, discDb libraries comprising a variety of combinations of antibodies against A and against B can be constructed.

In the present invention, a "linker" is not specifically limited as long as it does not interfere with expression of the antibody variable domains that are connected at both of its ends; the linker may or may not comprise restriction enzyme sites. Herein, a "long linker" means a linker of a size that enables the antibody heavy chain and light chain variable domains to be present as a scFv when the domains combined with the linker are expressed in a phage library. The length is not particularly limited, but preferably 30 bp to 150 bp, more preferably 36 bp to 90 bp, and most preferably 45 bp to 60 bp. Similarly, a "short linker" means a linker of a size that enables formation of a diabody (Db) when antibody heavy chain and light chain variable domains are combined with the linker and expressed. The length is not particularly limited, but preferably 6 bp to 27 bp, more preferably 9 bp to 21 bp, and most preferably 12 bp to 18 bp.

Furthermore, by placing appropriate restriction enzyme sites at the other ends of the gene encoding $V_L$a and $V_H$a, which are not connected to the linker, a fragment encoding $V_L$a-$V_H$b-$V_L$b-$V_H$a can be cutout, inserted into an appropriate expression vector, and expressed. The biological activity of such fragments can be used an index to screen for genes that encode desired diabodies. For example, in the above case where BamHI and AccIII are used in a phage antibody library directed against antigens A and B, a fragment may be cut out using another restriction enzyme, such as SfiI, and inserted into an appropriate vector, as shown in FIG. 1. Biological activity used as an index may be, for example, the activity of specifically binding an antigen. Depending on the type of antigen, it may also be an inhibitory activity, agonist activity, antagonist activity, or such. For example, to select an agonist bispecific diabody, a bispecific diabody library constructed using an antibody library against a cytokine receptor can be inserted into a vector such as a retrovirus vector, and infected into cells whose proliferation is dependent on a desired cytokine.

Methods common to the field of genetic engineering can be used to carry out procedures for constructing an expression system for the diabodies of the present invention, and for constructing recombinant vectors appropriate to the hosts (for example, Sambrook et al., Molecular Cloning, Cold Spring Harbor Laboratories (1989)). Host cells may be prokaryotic cells, such as bacteria, and eukaryotic cells, such as yeast, animal cells, insect cells, and plant cells, as long as the cells are capable of expressing the diabodies of the present invention. Mammalian cells are particularly preferred in view of glycosylation.

Expression vectors need to comprise units that regulate the transcription and translation of genetic information, such as promoters and terminators. For example, when *Escherichia* microorganisms such as *E. coli* are used as hosts, plasmids of the pBR or pUC series can be used as plasmid vectors, and any promoters selected from those such as lac, trp, tac, trc, λ phage PL, and PR can be used. Terminators may originate from trpA, phage, and rrnB ribosomal RNA. When the hosts are *Bacillus* microorganisms such as *B. subtilis*, plasmids such as those of the pUB110 and pC194 series can be used, and genes may be integrated into chromosomes in some cases. Promoters and terminators may be derived from apr, npr, amy, and such. Other prokaryotic cells include microorganisms such as *Pseudomonas* (e.g. *P. putida, P. cepacia*; pKT240 vectors, and such) *Brevibacteria* (e.g. *B. lactofermentum*; pAJ43), *Corynebacteria* (e.g. *C. glutamicum*; pCS11, pCB101), *Streptococcus* (e.g. pHV1301, pGK1), *Lactobatcillaceae* (e.g. pAMβ1), *Rhodcoccus* (e.g. plasmids isolated from *R. rhodochrous* (J. Gen. Microbiol. 138: 1003

(1992)), *Streptomyces* (e.g. *S. lividans, S. virginiae*; pIJ486, pKC1064, pUWL-KS), *Enterobacter, Erwinia, Kilebsiella, Proteus, Salmonella* (e.g. *S. typhimurium*), *Serratia* (e.g. *S. marcescans*), and *Shigella*.

Among expression systems utilizing eukaryotic microorganisms, a system using *Saccharomyces cerevisiae* as a host, and plasmids from YRp, YEp, YCp, and YIp series is known. Therein, promoters and terminators such as ADH, GAPDH, PHO, GAL, PGK, and ENO can be used. Other microorganisms used in the expression vector system of the present invention include *Kluyveromyces* (e.g. *K. lactis*; plasmids of the 2 µm, pKD1, pGKI1, and KARS series, and such), *Schizosaccharomyces* (e.g. *S. pombe*; pAUR224), *Zygosaccharomyces* (e.g. *Z. rouxii*; pSB3 and PH05 promoters from *S. cerevisiae*), *Hansenula* (e.g. *H. polymorpha*), *Pichia* (e.g. *P. pastoris*), *Candida* (e.g. *C. maltosa, C. tropicalis, C. utilis*, and *C. albicans*), *Aspergillus* (e.g. *A. oryzae, A. niger*), and *Trichoderma* (e.g. *T. reesei*).

In another embodiment, plant cells may be used as hosts. For example, host cells may be those from cotton, corn, potato, tomato, soybean, petunia, and tobacco. A particularly well-known system uses cells from *Nicotina tabacum*, which are cultured as a callus. To transform plant cells, expression vectors such as pMON530 are introduced into bacteria such as *Agrobacterium tumefaciens*. By infecting these bacteria into tobacco (*Nicotina tabacum*), desired polypeptides can be obtained from the tobacco leaves.

Cells from insects such as silkworms (*Bombyx mori*), mosquitoes (e.g. *Aede aegypti, Aedes albopictus*) and fruit flies (*Drosophila melanogaster*) can be used as hosts. For example, when using silkworms as hosts, DNAs encoding diabodies may be inserted into baculovirus vectors, these vectors may be used to infect silkworms, and desired polypeptides can be obtained from the silkworm body fluids (Nature 315: 592-594 (1985)).

Examples of expression vectors when using animal cells as hosts include pME18S (Med. Immunol. 20: 27-32 (1990)), pEF-BOS (Nucleic Acids Res. 18: 5322 (1990)), pCDM8 (Nature 329: 840-842 (1987)), pRSVneo, pSV2-neo, pcD-NAI/Amp (Invitrogen), pcDNAI, pAMoERC3Sc, pCDM8 (Nature 329: 840 (1987)), pAGE107 (Cytotechnology 3: 133 (1990)), pREP4 (Invitrogen), pAGE103 (J. Biochem. 101: 1307 (1987)), pAMoA, pAS3-3, pCAGGS (Gene 108: 193-200 (1991)), pBK-CMV, pcDNA3.1 (Invitrogen), and pZeoSV (Stratagene). Promoters may be cytomegalovirus IE gene promoter and enhancer, SV40 early promoter, a retrovirus LTR such as those from RSV, HIV, and MMLV, and gene promoters from animal cells such as metallothionein, β-actin, elongation factor-1, HSP genes, and such. Alternatively, viral vectors may be used as above. Viral vectors may be DNA viruses and RNA viruses such as retroviruses, adenoviruses, adeno-associated viruses, herpes viruses, vaccinia viruses, poxviruses, Simbu viruses, Sendai viruses, SV40, and HIV.

Host animal cells may be mouse myeloma cells (e.g. SP2/0, NS0) rat myeloma cells (e.g. YB2/0), mouse hybridoma cells, Namalwa cells (including KJM-1 cells), human embryonic kidney cells (e.g. 293 cells) human leukemia cells (e.g. BALL-1), CHO cells, COS cells (e.g. COS-1, COS-7), hamster embryonic kidney cells (e.g. BHK), mouse Sertoli cells (e.g. TM4), African green monkey kidney cells (e.g. VERO-76), HBT637 cells, HeLa cells, rabbit kidney cells (e.g. MDCK), human liver cells (e.g. HepG2), mouse mammary tumor cells (e.g. MMT060562), TRI cells, MRC cells, FS3 cells, etc.

Methods for introducing expression vectors depend on the type of host cell and vector, but any method can be used as long as it facilitates introduction of diabody-encoding DNA into cells. Vectors can be introduced into prokaryotic cells by methods utilizing calcium ions (Proc. Natl. Acad. Sci. USA 69: 2110 (1972)), protoplast (Unexamined Published Japanese Patent Application No. (JP-A) Sho 63-24829), electroporation (Gene 17: 107 (1982); Molecular & General Genetics 168: 111 (1979)), and such; introduced into yeast cells by using electroporation (Methods in Enzymology, 194: 182 (1990)), spheroplasts (Proc. Natl. Acad. Sci. USA 81: 4889 (1984)), lithium acetate (J. Bacteriol. 153: 163 (1983))), and such; introduced into plant cells by using *Agrobacterium* (Gene 23: 315 (1983); WO89/05859), sonication (WO91/00358), and such; and into animal cells by using electroporation (Cytotechnology 3: 133 (1990)), calcium phosphate (JP-A Hei 2-227075), lipofection (Proc. Natl. Acad. Sci. USA 84: 7413 (1987); Virology 52: 456 (1973)), co-precipitation with calcium phosphate, DEAE-dextran, direct injection of DNA using microcapillaries), and such.

Transformant cells obtained as described above can be cultured, for example, by the following methods:

Culture media for transformant cells of prokaryotes and eukaryotic microorganisms can be natural or synthetic, as long as the media facilitates efficient culture of the transformants, and comprises utilizable nutrients essential for growth, such as carbon and nitrogen sources, and inorganic salts. Culture may be carried out under aerobic or anaerobic conditions, and other conditions such as temperature, pH of the medium and duration of the culture can be determined appropriately by one skilled in the art, depending on the type of transformant. When using expression vectors equipped with inducible promoters, inducers may be added to the medium as necessary (for example, IPTG for the lac promoter, and IAA for the trp promoter).

When using insect cells as a host, the medium may be used such as TNM-FH medium (Pharmingen), Sf-900 II SFM (Life Technologies), ExCell400 and ExCell405 (JRH Biosciences), and Grace's Insect Medium (Nature 195: 788 (1962)). If necessary, antibiotics such as gentamicin may be added to the medium.

For animal cell transformants, a common medium can be used such as RPMI1640 (The Journal of American Medical Association 199: 519 (1967)), Eagle's MEM (Science 122: 501 (1952)), DMEM (Virology 8: 396 (1959)), and 199 medium (Proceeding of the Society for the Biological Medicine 73: 1 (1950)), or such media may be added with BSA and the like. Culture can be carried out under normal conditions such as pH 6 to 8, 30 to 40° C., and 5% $CO_2$. If necessary, antibiotics such as kanamycin and penicillin may be added to the medium.

The diabodies of the present invention, obtained as above, can be isolated using signal sequences from inside host cells, or from the culture medium if secreted into the extracellular space. They can then be purified as substantially pure polypeptides. Separation and purification of polypeptides can be performed by appropriately selecting or combining methods as necessary. Separation methods can be selected from those generally used, such as chromatography, filtration, ultrafiltration, salting out, solvent precipitation, solvent extraction, distillation, immunoprecipitation, SDS-polyacrylamide gel electrophoresis, isoelectric point focusing, dialysis, and recrystallization. Chromatography includes affinity chromatography, ion exchange chromatography, hydrophobic chromatography, gel filtration, reverse phase chromatography, absorption chromatography, and the like (Strategies for Protein Purification and Characterization: A Laboratory Course Manual, Daniel R. Marshak et al. eds., Cold Spring Harbor Laboratory Press (1996); Antibodies: A Laboratory Course Manual, Harlow and David Lane eds., Cold Spring Harbor Laboratory Press (1988)). Such chromatographies may be performed using liquid chromatographies such as HPLC, FPLC, and the like. In addition, since the diabodies of the present invention bind antigens, they may be purified by making use of this ability.

Furthermore, the present invention relates to genes that can be used in the above method of constructing scDb libraries, including (I) genes encoding two antibody variable domains that are connected with a linker comprising a restriction enzyme site, and (II) genes encoding two antibody variable domains, attached with restriction enzyme sites at both ends. The variable domains of the genes that provide sources for constructing the scDb libraries of the present invention preferably comprise heavy chain and light chain variable domains connected with a long linker, such that they are expressed as scFvs. An advantage of such genes is that expression vectors comprising (I) or (II) can be displayed on the surface of phage particles using a method such as fusion with bacteriophage coat proteins (Smith, Science 228: 1315 (1985); Scott and Smith, Science 249: 386 (1990); Cwirla et al., Proc. Natl. Acad. Sci. USA 8: 309 (1990); Devlin et al., Science 249: 404 (1990); Wells and Lowman, Curr. Opin. Struct. Biol. 2: 597 (1992); U.S. Pat. No. 5,223,409), and by selecting clones based on the phenotype of the peptides thus displayed, the genes that encode the clones can be simultaneously obtained.

The genes of (I) and (II), or antibody libraries comprising such genes, may be treated with restriction enzymes, and combined by ligation to obtain genes of the present invention that encode four antibody variable domains and comprise restriction enzyme sites between the first and second variable domains, and between the third and fourth variable domains. Bispecific single chain diabodies can be obtained by expressing such genes if both the first and second variable domains and the third and fourth variable domains are connected with a short linker, and the second and third variable domains are connected with a long linker, and further the variable domains are connected in the order of: heavy chain variable domain against antigen A, light chain variable domain against antigen B, heavy chain variable domain against antigen B, and light chain variable domain against antigen A.

The present invention comprises vectors and libraries comprising such genes, and peptides encoded by these genes.

In addition, the present invention provides methods for constructing antibody libraries or expression vectors, where the methods comprise:
(a) constructing antibody phage libraries in which light chain variable domains and heavy chain variable domains against antigens are connected with long linkers comprising two or more restriction enzyme sites,
(b) treating the above phage libraries, or genes comprising such variable domains and prepared from these phage libraries, with restriction enzymes, and
(c) performing self-ligation of the thus-obtained fragments to shorten the linkers between the variable domains.

These methods enable the methods for constructing scDb libraries of the present invention to be applied to the preparation of monospecific diabodies. For example, when phage libraries are constructed, two BamHI sites (underlined) can be designed within the linker, as below:

Next, the phage library, or genes comprising the variable domains prepared from the phage library (for example, phagemids concentrated from each library by panning and such, or genes amplified by PCR from the above phage library), are treated with BamHI, and self-ligated to reduce the length of the linker from 20 amino acids for scFvs to five amino acids, which is most suitable for diabodies ("GlyGlyGlyGlySer (SEQ ID NO: 6)" encoded by "GGTGGTGGTGGATCC (SEQ ID NO: 5)"). By inserting the resulting $V_L$-$V_H$ fragment comprising anti-receptor antibody into an appropriate expression vector, diabodies can be screened by using a biological activity as an index. For example, to select agonist diabodies, a diabody library constructed from an antibody library against a cytokine receptor may be inserted into retrovirus vectors, and infected into cells that are able to proliferate in a manner dependent on a desired cytokine.

The scDbs of the present invention are useful in clinical fields for immunodiagnosis, immunotherapy, and diagnosis based on immunoassays, similar to conventionally known multi-specific antibodies. For example, they can be used for a variety of therapeutic purposes such as for inducing cytotoxicity to kill tumor cells, as a vaccination adjuvant, for appropriately delivering drugs such as thrombolytic agents to in vivo targets, for ensuring the conversion of enzyme-activated prodrugs at target sites, for treating infectious diseases, for forming immune complexes at cell surface receptors, and for delivering immunotoxins to target cells such as tumor cells.

Pharmaceutical compositions used for such therapeutic purposes, which comprise diabodies of the present invention, may be formulated by mixing with suitable pharmaceutically acceptable carriers and solvents, if necessary, that are inactive against the diabodies. For example, sterilized water, saline, stabilizers, vehicles, antioxidants (e.g. ascorbic acid), buffers (e.g. phosphate, citrate, other organic acids), preservatives, detergents (e.g. PEG, Tween), chelating agents (e.g. EDTA), and binders may be used. Alternatively, they may comprise other low molecular weight polypeptides, proteins such as serum albumin, gelatin and immunoglobulins, amino acids such as glycine, glutamine, asparagine, arginine, and lysine, carbohydrates and sugars such as polysaccharides and monosaccharides, and sugar alcohol such as mannitol and sorbitol. When prepared as an aqueous solution for injection, saline and isotonic solutions comprising glucose and other adjunctive agents such as D-sorbitol, D-mannose, D-mannitol, and sodium chloride may be used. In addition, an appropriate solubilizing agent such as alcohol (e.g. ethanol), polyalcohol (e.g. propylene glycol, PEG), and non-ionic detergents (e.g. polysorbate 80, HCO-50) may be used in combination.

If necessary, diabodies of the present invention may be encapsulated in microcapsules (microcapsules made of hydroxycellulose, gelatin, polymethylmethacrylate, and the like), and made into components of colloidal drug delivery systems (liposome, albumin microsphere, microemulsion, nano-particles, and nano-capsules) (refer to, for example, "Remington's Pharmaceutical Science 16th edition", Oslo Ed. (1980)). Moreover, methods for making sustained-release drugs are known, and these can be applied for the diabodies of the present invention (Langer et al., J. Biomed. Mater. Res. 15: 167-277 (1981); Langer, Chem. Tech. 12:

```
GlyGlyGlyGlySerGlyGlyGlyGlySerGlyGlyGlyGlySerGlyGlyGlyGlySer  (SEQ ID NO: 4)
```

```
GGTGGTGGTGGATCCGGTGGTGGTGGTTCTGGCGGCGGCGGCTCCGGAGGTGGTGGATCC  (SEQ ID NO: 3)
```

98-105 (1982); U.S. Pat. No. 3,773,919; EP Patent Application No. 58,481; Sidman et al., Biopolymers 22: 547-556 (1983); EP: 133,988).

Administration to patients may be preferably performed by injections or intravenous drips; for example, in addition to intra-arterial injections, intravenous injections, and subcutaneous injections, methods known to one skilled in the art may be used, such as administrating intranasally, intrabronchially, intramuscularly, percutaneously, or orally. Doses may vary depending on various factors, including patient body weight and age, type of disease, symptoms, and administration method, but those skilled in the art are able to appropriately select suitable doses.

In addition, genes encoding diabodies of the present invention may be used for gene therapy by cloning into vectors for such use. Such vectors can be administered by direct injection using naked plasmids, and also by packaging in liposomes, producing as a variety of viral vectors such as retrovirus vectors, adenovirus vectors, vaccinia virus vectors, poxvirus vectors, adenoassociated virus vectors, and HVJ vector (Adolph, "Virus Genome Methods", CRC Press, Florida (1996)), or coating onto carrier beads such as colloidal gold particles (e.g. WO93/17706). However, any method can be used for administration as long as the diabodies are expressed in vivo and exercise their function. Preferably, a sufficient dose may be administered by a suitable parenteral route (such as injecting intravenously, intraventricularly, subcutaneously, percutaneously, or into adipose tissues or mammary glands, inhalation, intramuscular injection, infusion, gas-induced particle bombardment (using electron gun and such), or through mucosa such as by nose drops). Alternatively, genes encoding diabodies of the present invention may be administered into, for example, blood cells bone marrow cells ex vivo using liposome transfection, particle bombardment (U.S. Pat. No. 4,945,050), or viral infection, and the cells may be reintroduced into animals.

In addition, the diabodies of the present invention may be used for enzyme immunoassays. For this, one of the antibody variable domains of a diabody may be designed to recognize an epitope that does not interfere with the enzymatic activity of the enzyme, and the other arm can be designed to recognize and bind to a carrier that binds an antibody. For example, diabodies that recognizes IgG, ferritin, HRP, and hormones may be used for such analysis.

In addition, the diabodies of the present invention may be used for in vivo and in vitro immunodiagnosis of a variety of diseases. For example, one of the antibody variable domains of a diabody can be designed to recognize an antigen that is specific to tumor cells, and the other arm can be designed to bind a detectable marker. Detectable markers include radioisotopes (e.g. $^{3}H$, $^{14}C$, $^{32}P$, $^{35}S$, and $^{125}I$), fluorescent dyes (e.g. fluorescein, luciferin), chemiluminescent compounds (e.g. isothiocyanate, rhodamine), and generally used enzymes such as alkaline phosphatase, β-galactosidase, and HRP. Binding of diabodies to these compounds and detection can be performed according to known methods (Hunter et al., Nature 144: 945 (1962); David et al., Biochemistry 13: 1014 (1974); Pain et al., J. Immunol. Meth. 40: 219 (1981); Nygen, J. Histochem. Cytochem. 30: 407 (1982)).

Such diabodies of the present invention capable of reacting with detectable compounds can be used in a variety of assays, including competitive binding assays, direct and indirect sandwich immunoassays (e.g. ELISA), and immunoprecipitation assays (Zola, "Monoclonal Antibodies: A Manual of Techniques", 147-158, CRC Press Inc. (1987)).

INDUSTRIAL APPLICABILITY

The present invention provides novel methods for constructing bispecific scDb libraries. By using the methods of this invention, bispecific scDb libraries can be collectively constructed from scFv phage libraries without troublesome procedures. The present invention also provides methods for collectively transferring antibody clones, which have been concentrated from phage antibody libraries by panning and such, to expression vectors used in animal cells.

The invention claimed is:

1. A method for constructing a single chain diabody library, the method comprising:
   (a) providing a first phage antibody library that encodes single chain antibodies that bind to a first antigen, each member of the library comprising a nucleotide sequence encoding a light chain variable domain and a nucleotide sequence encoding a heavy chain variable domain, wherein the nucleotide sequence encoding the light chain variable domain is connected to the nucleotide sequence encoding the heavy chain variable domain by a first nucleotide linker of 45 to 60 base pairs encoding a peptide linker and comprising a cleavage site for a first restriction enzyme and a cleavage site for a second restriction enzyme that is different from the first restriction enzyme;
   (b) providing a second phage antibody library that encodes single chain antibodies that bind to a second antigen, each member of the library comprising (i) a nucleotide sequence encoding a light chain variable domain and (ii) a nucleotide sequence encoding a heavy chain variable domain, wherein the nucleotide sequence of (i) is connected to the nucleotide sequence of (ii) by a second nucleotide linker of 45 to 60 base pairs encoding a peptide linker, and wherein the end of the nucleotide sequence of (i) that is distal to the second nucleotide linker comprises a cleavage site for the first restriction enzyme, and the end of the nucleotide sequence of (ii) that is distal to the second nucleotide linker comprises a cleavage site for the second restriction enzyme;
   (c) treating the first library with the two restriction enzymes to cleave the two sites within the first nucleotide linker;
   (d) treating the second library with the two restriction enzymes to produce a plurality of fragments, each fragment having a cleaved restriction site at its 5' end and a cleaved restriction site at its 3' end, wherein each fragment comprises the nucleotide sequence of (b)(i) connected to the nucleotide sequence of (b)(ii) via the second nucleotide linker; and (e) ligating the cleaved product of (c) with the plurality of fragments of (d) to construct a third library of nucleic acids, each encoding a single polypeptide chain comprising both the light and heavy chain variable domains of (a) and the light and heavy chain variable domains of (b), wherein the light and heavy chain variable domains of (b) are inserted between the light and heavy chain variable domains of (a) and are separated from the light and heavy chain variable domains of (a) by a pair of short linkers, each encoded by 6 to 27 base pairs, wherein the lengths of the short linkers are determined by the locations of the cleavage sites for the first and second restriction enzymes in the first nucleotide linker of (a).

2. A method for producing a construct encoding a single chain diabody, the method comprising:
(a) providing a first nucleic acid that encodes a single chain antibody polypeptide that binds to a first antigen and comprises a nucleotide sequence encoding a light chain variable domain and a nucleotide sequence encoding a heavy chain variable domain, wherein the nucleotide sequence encoding the light chain variable domain is connected to the nucleotide sequence encoding the heavy chain variable domain by a first nucleotide linker of 45 to 60 base pairs encoding a peptide linker and comprising a cleavage site for a first restriction enzyme and a cleavage site for a second restriction enzyme that is different from the first restriction enzyme;
(b) providing a second nucleic acid that encodes a single chain antibody polypeptide that binds to a second antigen and comprises (i) a nucleotide sequence encoding a light chain variable domain and (ii) a nucleotide sequence encoding a heavy chain variable domain, wherein the nucleotide sequence of (i) is connected to the nucleotide sequence of (ii) by a second nucleotide linker of 45 to 60 base pairs encoding a peptide linker, and wherein the end of the nucleotide sequence of (i) that is distal to the second nucleotide linker comprises a cleavage site for the first restriction enzyme, and the end of the nucleotide sequence of (ii) that is distal to the second nucleotide linker comprises a cleavage site for the second restriction enzyme;
(c) treating the first nucleic acid with the two restriction enzymes to cleave the two sites within the first nucleotide linker;
(d) treating the second nucleic acid with the two restriction enzymes to produce a fragment having a cleaved restriction site at its 5' end and a cleaved restriction site at its 3' end, wherein the fragment comprises the nucleotide sequence of (b)(i) connected to the nucleotide sequence of (b)(ii) via the second nucleotide linker; and
(e) ligating the cleaved product of (c) with the fragment of (d) to construct a third nucleic acid encoding a single polypeptide chain comprising both the light and heavy chain variable domains of (a) and the light and heavy chain variable domains of (b), wherein the light and heavy chain variable domains of (b) are inserted between the light and heavy chain variable domains of (a) and are separated from the light and heavy chain variable domains of (a) by a pair of short linkers, each encoded by 6 to 27 base pairs; wherein the lengths of the short linkers are determined by the locations of the cleavage sites for the first and second restriction enzymes in the first nucleotide linker of (a); and wherein the third nucleic acid either is an expression vector or is inserted into an expression vector subsequent to the ligating step.

3. A method for constructing an antibody library, the method comprising:
(a) providing a phage antibody library that encodes single chain antibodies that bind to an antigen, each member of the library comprising a first nucleotide sequence encoding a light chain variable domain and a second nucleotide sequence encoding a heavy chain variable domain, both domains being directed against the same antigen, wherein the first nucleotide sequence is connected to the second nucleotide sequence by a nucleotide linker of 45 to 60 base pairs encoding a peptide linker and comprising two or more cleavage sites for a restriction enzyme;
(b) treating the library with the restriction enzyme to cleave the two or more sites within the nucleotide linker; and
(c) self-ligating the cleaved product of (b) to generate a second antibody library, each member of the second library comprising the first and the second nucleotide sequences joined by a nucleotide linker that is shorter than the nucleotide linker in the library of (a).

4. The method of claim 1, wherein the amino acid sequence of the peptide linker of (a) and the amino acid sequence of the peptide linker of (b) each is 15 to 20 amino acids in length, and each contains one or more copies of the sequence GlyGlyGlyGlySer (SEQ ID NO: 6).

5. The method of claim 1, wherein the amino acid sequence of the peptide linker of (a) and the amino acid sequence of the peptide linker of (b) each is 15 to 20 amino acids in length, and each contains the sequence [GlyGlyGlyGlySer (SEQ ID NO: 6)]n, wherein n is 3 or 4.

6. The method of claim 1, wherein the amino acid sequence of the peptide linker of (a) and the amino acid sequence of the peptide linker of (b) each is [GlyGlyGlyGlySer (SEQ ID NO: 6)]$_4$.

7. The method of claim 2, wherein the amino acid sequence of the peptide linker of (a) and the amino acid sequence of the peptide linker of (b) each is 15 to 20 amino acids in length, and each contains one or more copies of the sequence GlyGlyGlyGlySer (SEQ ID NO: 6).

8. The method of claim 2, wherein the amino acid sequence of the peptide linker of (a) and the amino acid sequence of the peptide linker of (b) each is 15 to 20 amino acids in length, and each contains the sequence [GlyGlyGlyGlySer (SEQ ID NO: 6)]n, wherein n is 3 or 4.

9. The method of claim 2, wherein the amino acid sequence of the peptide linker of (a) and the amino acid sequence of the peptide linker of (b) each is [GlyGlyGlyGlySer (SEQ ID NO: 6)]$_4$.

10. The method of claim 3, wherein the amino acid sequence of the peptide linker is 15 to 20 amino acids in length and contains one or more copies of the sequence GlyGlyGlyGlySer (SEQ ID NO: 6).

11. The method of claim 3, wherein the amino acid sequence of the peptide linker is 15 to 20 amino acids in length, and contains the sequence [GlyGlyGlyGlySer (SEQ ID NO: 6)]n, wherein n is 3 or 4.

12. The method of claim 3, wherein the amino acid sequence of the peptide linker is [GlyGlyGlyGlySer (SEQ ID NO: 6)]$_4$.

* * * * *